United States Patent
Kishima et al.

(10) Patent No.: US 6,792,812 B2
(45) Date of Patent: Sep. 21, 2004

(54) METHOD AND APPARATUS FOR LAYERED STRUCTURE BREAKING STRENGTH ESTIMATION

(75) Inventors: Yoshio Kishima, Saitama (JP); Masakazu Otake, Yamagata (JP)

(73) Assignees: Diapola Wintes Co., Ltd., Saitama (JP); Mekong Co., Ltd., Yamagata (JP)

( * ) Notice: Subject to any disclaimer, the term of this patent is extended or adjusted under 35 U.S.C. 154(b) by 228 days.

(21) Appl. No.: 10/033,434

(22) Filed: Dec. 26, 2001

(65) Prior Publication Data

US 2002/0095996 A1 Jul. 25, 2002

(30) Foreign Application Priority Data

Dec. 27, 2000 (JP) ........................................ 2000-396343

(51) Int. Cl.⁷ ............................ G01N 3/24; G01F 17/00
(52) U.S. Cl. ...................... 73/845; 73/150 R; 73/150 A
(58) Field of Search ............................. 73/845, 150 A, 73/150 R

(56) References Cited

U.S. PATENT DOCUMENTS

| | | | | |
|---|---|---|---|---|
| 4,934,185 A | * | 6/1990 | Nishiyama et al. | ........ 73/150 A |
| 5,101,655 A | * | 4/1992 | Mueller | ........................... 73/7 |
| 5,333,494 A | * | 8/1994 | Kishima et al. | .............. 73/104 |
| 6,050,139 A | * | 4/2000 | Bousfield et al. | ......... 73/150 A |
| 6,295,866 B1 | * | 10/2001 | Yamamoto et al. | ........... 73/105 |

* cited by examiner

Primary Examiner—Edward Lefkowitz
Assistant Examiner—Lilybett Martir
(74) Attorney, Agent, or Firm—Jordan and Hamburg LLP

(57) ABSTRACT

Method for layered structure breaking strength estimation in which an edge of a cutting blade is inserted into an upper layer of the structure and the cutting blade is moved substantially in parallel with an interface between the upper layer and a lower layer of the structure while automatically controlling a depth of the cutting blade to a depth slightly higher than the interface. A force exerted on the cutting blade substantially in parallel with the interface is measured. An apparatus for performing the method is also disclosed.

14 Claims, 5 Drawing Sheets ized or Japanese Industrial
METHOD AND APPARATUS FOR LAYERED STRUCTURE BREAKING STRENGTH ESTIMATION

BACKGROUND OF THE INVENTION

1. Field of the Invention

The present invention relates to a layered structure breaking strength estimating method and apparatus, more particularly to a method and apparatus for estimating the breaking strength of a layered structure which includes an upper layer and a lower layer.

2. Description of the Related Art

Among known methods of estimating the breaking strength of a layered structure which includes an upper layer and a lower layer are a peel strength test and a chess-board breaking strength test specified in the ISO (International Organization for Standardization) or Japanese Industrial Standard.

Such known methods are however may hardly estimate a difference in the breaking strength between the two, upper and lower, layers when the two layers are too high in the bonding strength to be separated from each other.

It is hence an object of the present invention to provide a method of layered structure breaking strength estimation which provides a new criterion for evaluating a difference in the breaking strength when the bonding strength between the two, upper and lower, layers is high.

SUMMARY OF THE INVENTION

As a first aspect of the present invention, a method and an apparatus for layered structure breaking strength estimation is characterized by inserting the edge of a cutting blade into the upper layer of the structure, moving the cutting blade substantially in parallel with the interface between the upper layer and the lower layer while the depth of the cutting blade being controlled to such a depth slightly higher than the interface, and measuring a force exerted on the cutting blade substantially in parallel with the interface.

In the above arrangement, the cutting blade may be moved when the layered structure remains stationary. Alternatively, the layered structure may be moved when the cutting blade remains stationary or both may be moved.

The force required for cutting close to the interface between the two layers in the layered structure may be used as a criterion for determining the breaking strength of the layered structure. However, if the cutting location is too shallow over the interface, measurement of the breaking strength can be biased to the upper layer. If the cutting location is too deep, measurement of the breaking strength can be biased to the lower layer. When the upper layer and the lower layer are overlapped or the interface is undulated, the position of the interface will hardly be identified. It would hence be uncertain for examining the breaking strength of the layered structure to determine the depth to be cut.

In view of the above drawbacks, we, the inventors, have studied through continuous experiments and found that the breaking strength of a layered structure is favorably measured, even when the bonding strength is relatively high or the location of the interface is unclear, by a manner in which as the cutting blade is driven along the interface (which means a virtual plane or not undulated curve extending in the middle of a overlapped portion of the two, upper and lower, layers when the two layers are overlapped, or means an averaged virtual plane or not undulated curve when the interface is undulated) and a depth is controlled to such a depth that a cutting piece stays on the cutting blade, thus creating a breakage at the weakest region of the layered structure close to the interface.

The layered structure breaking strength estimating method and apparatus of the first aspect of the present invention is implemented in which while the cutting blade is inserted into the upper layer, maintained at a setting depth slightly higher than the interface with its edge continuously holding directly a cutting piece, and moved substantially in parallel with the interface, a force exerted on the cutting blade substantially in parallel with the interface is measured and used as the criterion for estimating the breaking strength of the layered structure. This allows any layered structure which is relatively high in the bonding strength or has an interface located at an obscure depth to be successfully examined for its breaking strength.

The cutting blade with its edge holding a cutting piece may be monitored using an optical enlarging device.

As the force exerted on the cutting blade substantially in parallel with the interface alternates between increase and decrease, its maximum, minimum, amplitude, cycle, and average may be used as the criteria for examining the breaking strength.

As a second aspect of the present invention, a method and an apparatus for layered structure breaking strength estimation is characterized by inserting the edge of a cutting blade into the upper layer of the structure and moving the cutting blade substantially in parallel with the interface between the upper layer and the lower layer, measuring a force exerted on the cutting blade substantially in parallel with the interface, moving the cutting blade substantially in parallel with the interface while the depth of the cutting blade being controlled to such a depth where the force alternates between increase and decrease.

In the above arrangement, the cutting blade may be moved when the layered structure remains stationary. Alternatively, the layered structure may be moved when the cutting blade remains stationary or both may be moved.

The force required for cutting close to the interface between the two layers in the layered structure may be used as a criterion for determining the breaking strength of the layered structure. However, if the cutting location is too shallow over the interface, measurement of the breaking strength can be biased to the upper layer. If the cutting location is too deep, measurement of the breaking strength can be biased to the lower layer. When the upper layer and the lower layer are overlapped or the interface is undulated, the position of the interface will hardly be identified. It would hence be uncertain for examining the breaking strength of the layered structure to determine the depth to be cut.

In view of the above drawbacks, we, the inventors, have studied through continuous experiments and found that the breaking strength of a layered structure is favorably measured by a manner in which as the cutting blade is inserted at its edge into the upper layer and driven along and substantially in parallel with the interface (which means a virtual plane or not undulated curve extending in the middle of a overlapped portion of the two, upper and lower, layers when the two layers are overlapped, or means an averaged virtual plane or not undulated curve when the interface is undulated), it is favorably controlled to such a desired depth that the force exerted on the cutting blade alternates between increase and decrease. More specifically, this manner allows the force exerted substantially in parallel with the interface to be increased until the layered structure is broken up. At the moment when the force reaches a some great level, the layered structure is broken up at its weakest location close to the interface and its physical resistance is sharply declined thus offsetting the force exerted substantially in parallel with the interface. As this action is repeated, the layered structure is broken up at its weakest location close to the interface in cycles. Accordingly, the breaking strength of the layered structure can be measured even when the bonding strength is relatively high or the location of the interface is obscure.

The layered structure breaking strength estimating method and apparatus of the second aspect of the present invention is implemented in which while the cutting blade is inserted into the upper layer, maintained at such a setting depth that the force exerted on the cutting blade substantially in parallel with the interface alternates between increase and decrease, and moved substantially in parallel with the interface, a force exerted on the cutting blade substantially in parallel with the interface is measured and used as the criterion for estimating the breaking strength of the layered structure. This allows any layered structure which is relatively high in the bonding strength or has an interface located at an obscure depth to be successfully examined for its breaking strength.

The force exerted on the cutting blade may be measured using a load cell.

As the force exerted on the cutting blade substantially in parallel with the interface alternates between increase and decrease, its maximum, minimum, amplitude, cycle, and average may be used as the criteria for examining the breaking strength.

As a third aspect of the present invention, the method and apparatus for layered structure breaking strength estimation defined in above aspects is modified wherein the force exerted on the cutting blade substantially in parallel with the interface, a force exerted on the cutting blade substantially vertical to the interface, and the depth of the cutting blade are expressed in the form of a graphic profile of change with time.

The layered structure breaking strength estimating method and apparatus of the third aspect of the present invention allows the three factors of the cutting blade during the cutting action to be expressed in graphic profiles thus clarifying the relationship between the factors.

The force exerted on the cutting blade may be measured using a load cell. The depth of the cutting blade may be measured using a displacement meter.

As a fourth aspect of the present invention, the method and appratus for layered structure breaking strength estimation described above is modified wherein the unit of displacement of the cutting blade for determining the depth of the edge of the cutting blade is not greater than 2 micro meter.

If the unit of displacement of the cutting blade is greater than 2 $\mu$m, fine depth controll can be set with much difficulty.

The layered structure breaking strength estimating method and appratus of the fourth aspect of the present invention is implemented with the unit of displacement not greater than 2 $\mu$m, thus allowing the depth to be set accurately.

DETAILED DESCRIPTION OF THE PREFERRED EMBODIMENTS

One embodiment of the present invention will be described referring to the relevant drawings. The present invention is not limited to the embodiment.

Figure 1:
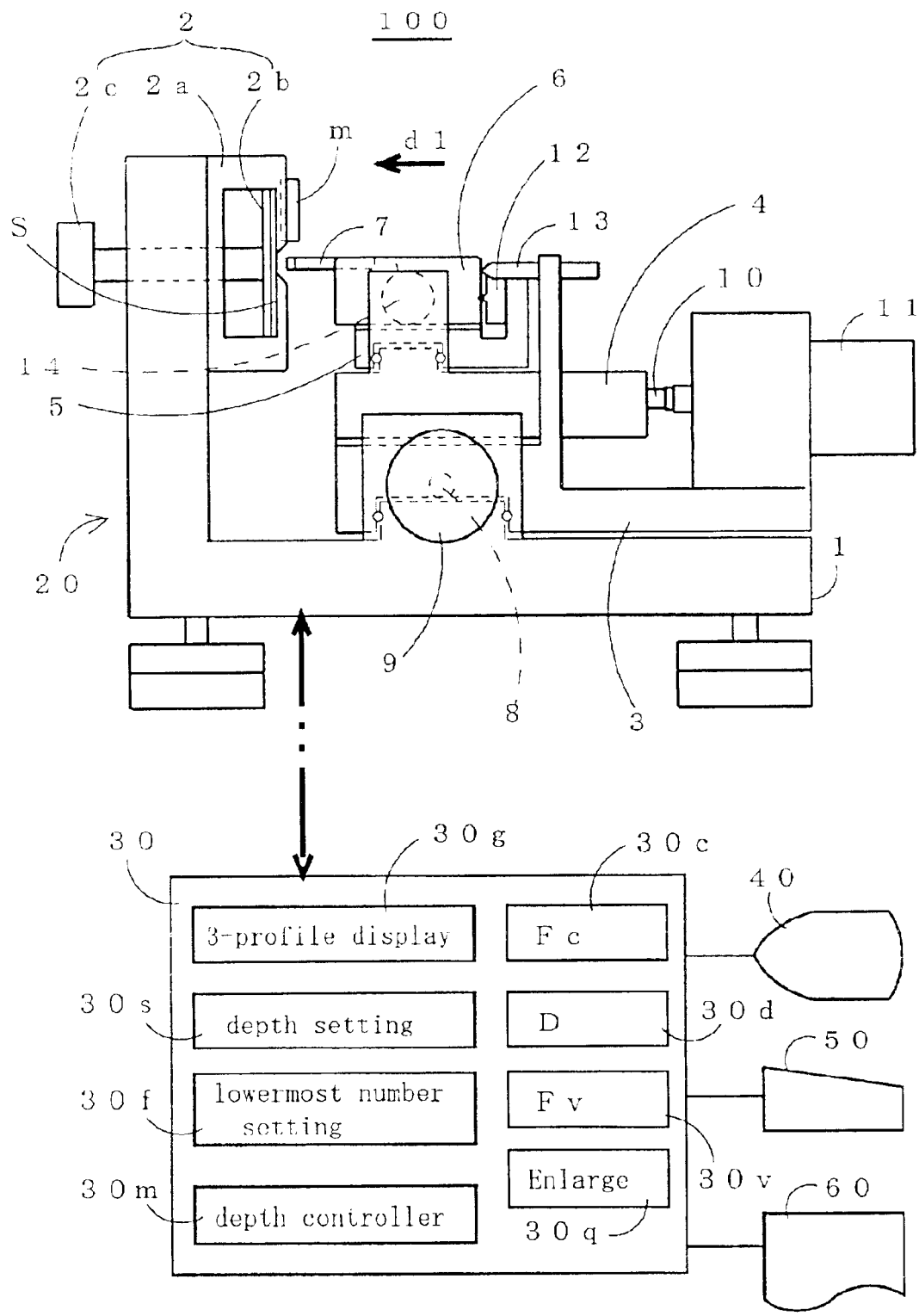
FIG. 1 is a front view of a layered structure breaking strength estimating apparatus showing one embodiment of the present invention.
Figure 2:
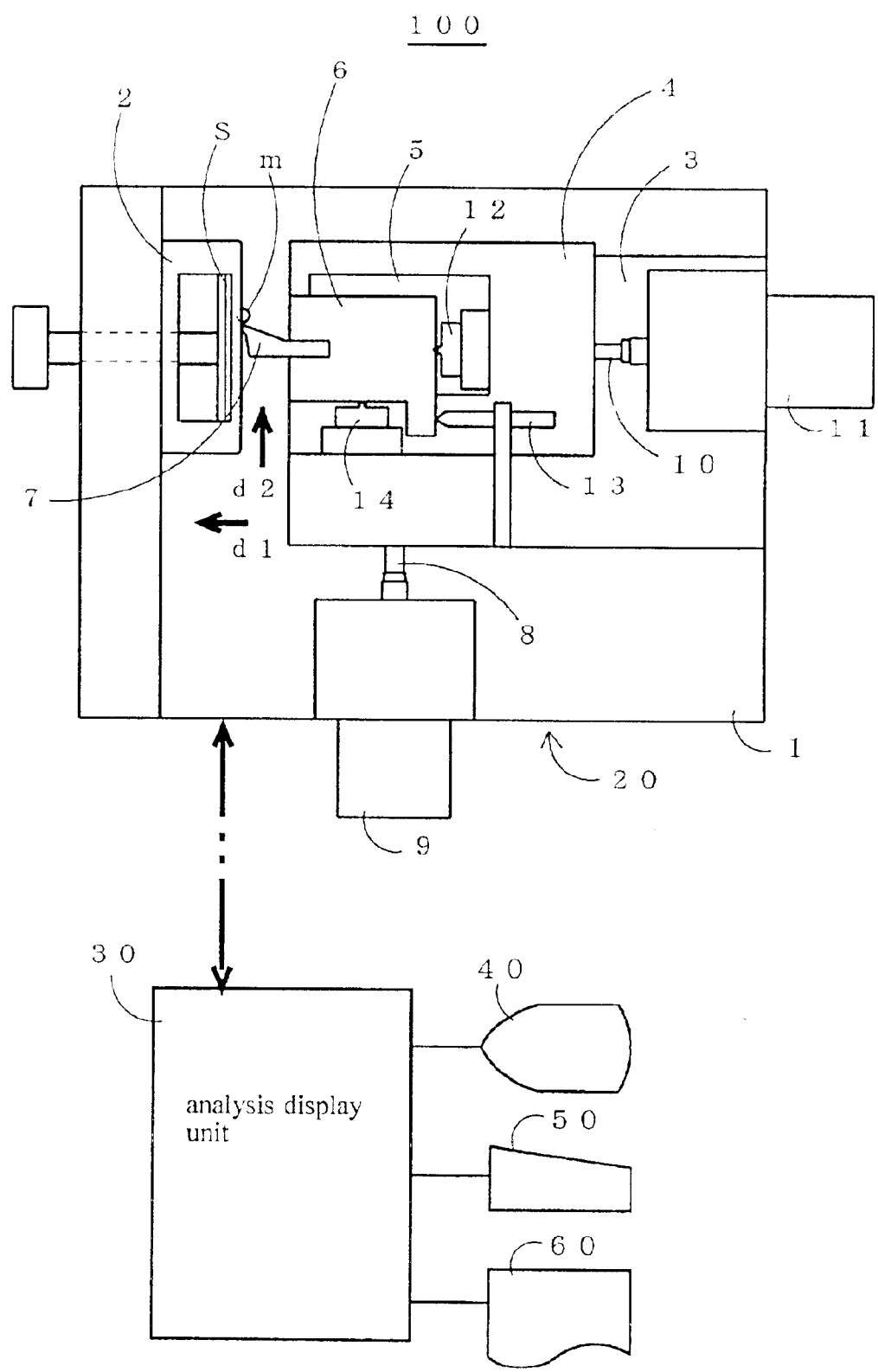
FIG. 2 is a top view of the layered structure breaking strength estimating apparatus of the embodiment of the present invention.
Figure 3:
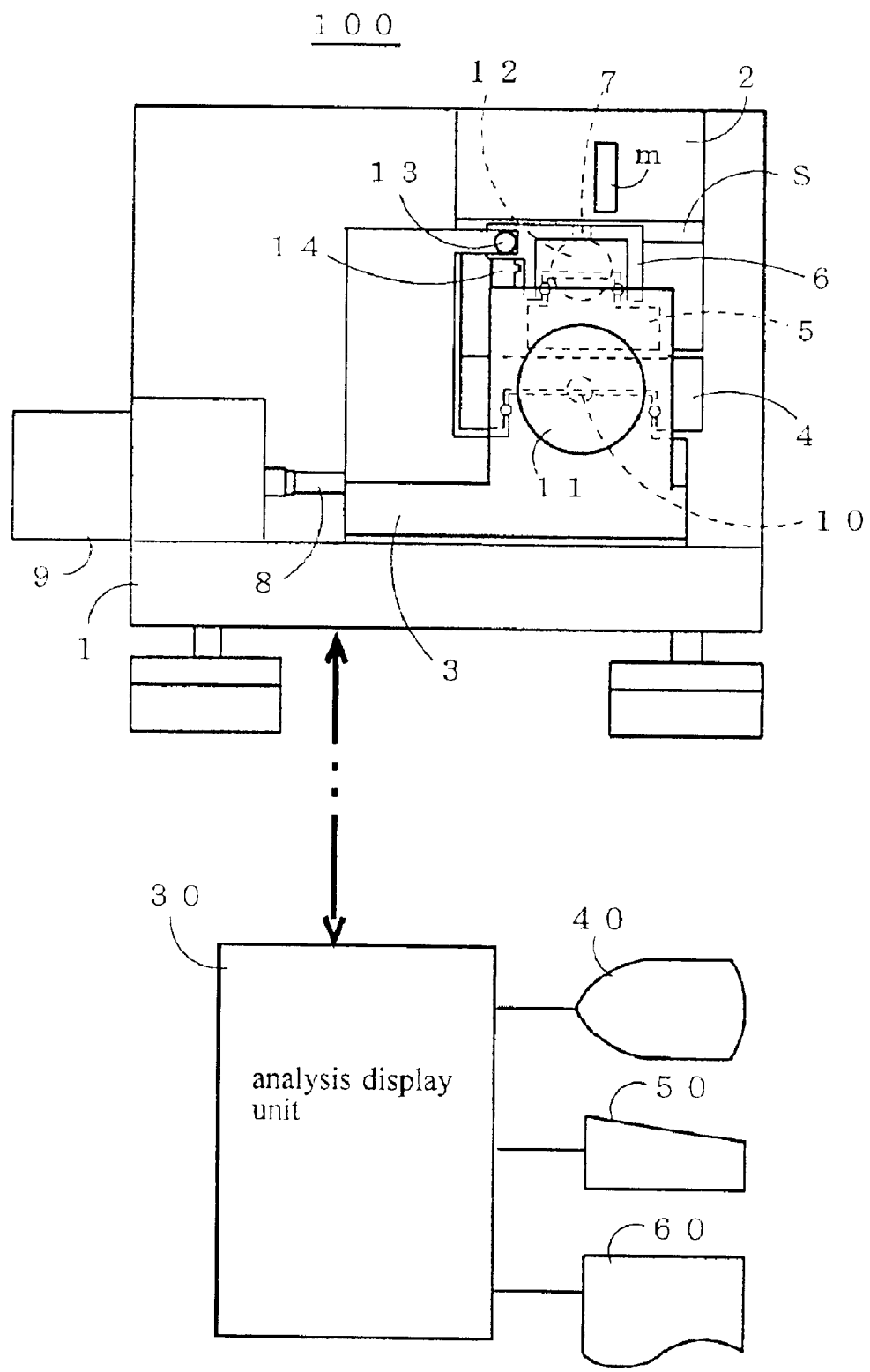
FIG. 3 is a right side view of the layered structure breaking strength estimating apparatus of the embodiment of the present invention.

FIG. 1 is a front view of a layered structure breaking strength estimating apparatus. FIG. 2 and FIG. 3 are a right side view and a left side view of the same respectively.

A layered structure breaking strength estimating apparatus denoted by 100 comprises a sample cutting unit 20, an analysis display unit 30, a monitor 40, an input unit 50, and a printer 60.

The sample cutting unit 20 includes a bed 1, a sample holder 2 mounted to the bed 1, a transverse slide way 3 supported on the bed 1 for sliding movement in a second direction d2 (See FIG. 2), a longitudinal slide way 4 supported on the traverse slide way 3 for sliding movement in a first direction d1, a transverse load slide way 5 supported on the longitudinal slide way 4 for sliding movement in the second direction d2 (See FIG. 2), a longitudinal load slide way 6 supported on the transverse load slide way 5 for sliding movement in the first direction d1, a cutting blade 7 held to the longitudinal load slide way 6, a transverse driving motor 9 mounted on the bed 1 for driving a transverse ball screw 8 to move the transverse slide way 3 in the second direction d2 (FIG. 2), a longitudinal driving motor 11 mounted on the transverse slide way 3 for driving a longitudinal ball screw 10 to move the longitudinal slide way 4 in the first direction d1, a longitudinal load cell 12 for measuring the longitudinal load Fv exerted on the cutting blade 7 in the first direction d1, a displacement meter 13 for measuring the cutting depth D in the first direction d1, a transverse load cell 14 for measuring the transverse load Fc exerted on the cutting blade 7 in the second direction d2, and a camera m mounted to the sample holder 2.

The first direction d1 and the second direction d2 extend along a horizontal plane and intersect each other at a right angle.

The sample holder 2 includes a front-side hold-down 2a for holding the front side of a sample S through an access opening provided in the cutting blade 7, a back-side hold-down 2b for pressing the back side of the sample S against the front-side hold-down 2a, and a hold-down screw 2c for tightening the back-side hold-down 2b to the front-side hold-down 2a.

The sample holder 2 can securely hold the sample S while pressing against its back side. More particularly, the sample S is held at its front side in parallel with the blade line (a straight line along the blade edge) of the cutting blade 7 even if its back side is undulated. The sample S can properly be held regardless of the shape of the sample S.

The analysis display unit 30 includes an Fv display 30v for displaying measurements of the longitudinal load Fv measured by the longitudinal load cell 12 and their profile of change with time on the monitor 40, a D display 30d for displaying measurements of the cutting depth D measured by the displacement meter 13 and their profile of change with time on the monitor 40, an Fc display 30c for displaying measurements of the transverse load Fc measured by the transverse load cell 14 and their profile of change with time on the monitor 40, an enlargement display 30q for displaying on the monitor 40 an enlarged view of the cutting condition pictured by the camera m, a three-profile simultaneous display 30g for displaying three profiles of change with time of the longitudinal load Fv, the cutting depth D, and the transverse load Fc at once on the monitor 40, a cutting depth setting 30s for presetting the cutting depth, a longitudinal load lowermost number setting 30f for presetting the number of lowermost points of the longitudinal load, and a cutting depth controller 30m for controlling the cutting depth D.

The cutting depth controller 30m controls the cutting depth to a setting level predetermined by the cutting depth setting 30s. Also, the cutting depth controller 30m controls the cutting depth to cut in to the depth until the number of the lowermost points on the profile of change of the longitudinal load Fv with time reaches to the value predetermined by the longitudinal load lowermost number setting 30f and keeps the depth. Also, upon receiving an instruction for automatic transverse load tracing action from the input unit 50, the cutting depth controller 30m controls the cutting depth to such a level that the transverse load Fc alternates between increase and decrease. Moreover, in response to an instruction for increasing or decreasing the cutting depth from the input unit 50, the cutting depth controller 30m increases or decreases the cutting depth by a unit distance at each instruction. The unit distance may be 2 μm.

The sample S may be analyzed by the layered structure breaking strength estimating apparatus 100 using one of the following procedures.

Figure 4:
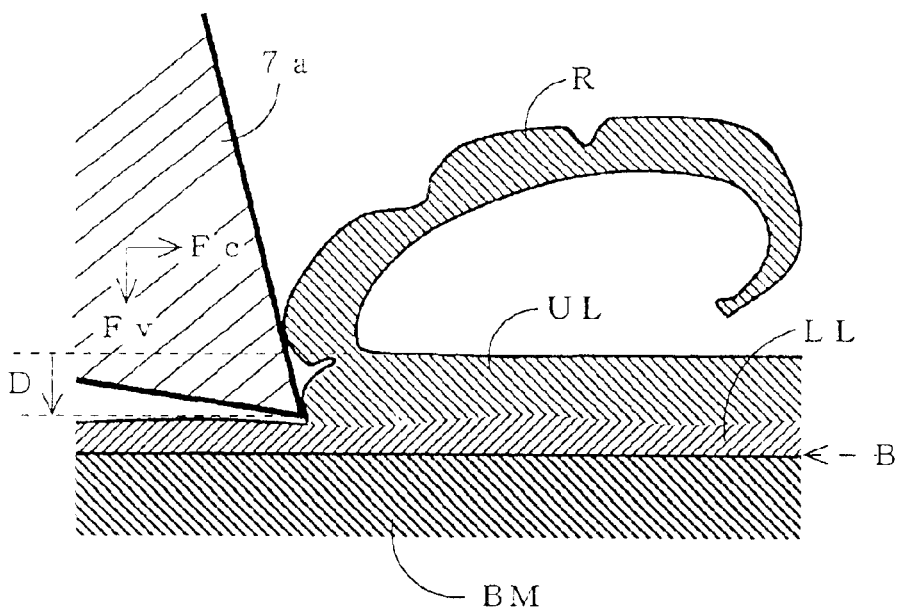
FIG. 4 is an enlarged cross sectional view of a cutting condition where peeling is not progressed.
Figure 5:
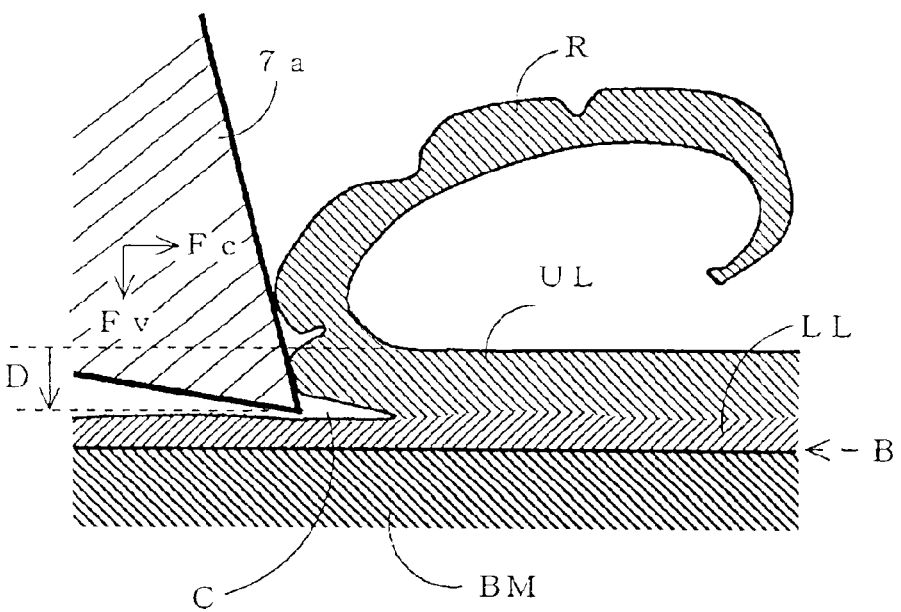
FIG. 5 is an enlarged cross sectional view of the cutting condition where peeling and breakage is promptly progressed.

First Procedure
(1) The sample S is held by the sample holder 2 with its front side extending vertical.
(2) The longitudinal slide way 4 is moved in the first direction d1 by a combination action of the longitudinal driving motor 11 and the longitudinal ball screw 10. This allows the longitudinal load slide way 6 to move in the first direction d1 and thus the cutting blade 7 to cut into the sample S. While its cutting condition being viewed in an enlarged view on the monitor 40, the cutting blade 7 is advanced until its edge 7a reaches slightly upper than the interface B between the upper layer (consisting of a finish coating UL and a base coating LL) and the lower layer (a substrate BM) as shown in FIGS. 4 and 5.
(3) The transverse slide way 3 is moved in the second direction d2 by a combination action of the transverse driving motor 9 and the transverse ball screw 8. As a result, the cutting blade 7 advances in the second direction d2.
(4) While its cutting condition being viewed in an enlarged view on the monitor 40, the cutting blade 7 is shifted in the second direction d2 with its depth manually adjusted (to be deep or shallow in steps of 2 μm as controlled by the action of the input unit 50) so that a cutting scrap remains directly on its edge 7a as shown in FIGS. 4 and 5.
(5) As the longitudinal load Fv, the cutting depth D, and the transverse load Fc measured at the above process (4) are expressed in a graphic profile of change with time and displayed on the monitor 40 or plotted down by a printer 60, they can be examined for further estimation.

Figure 6:
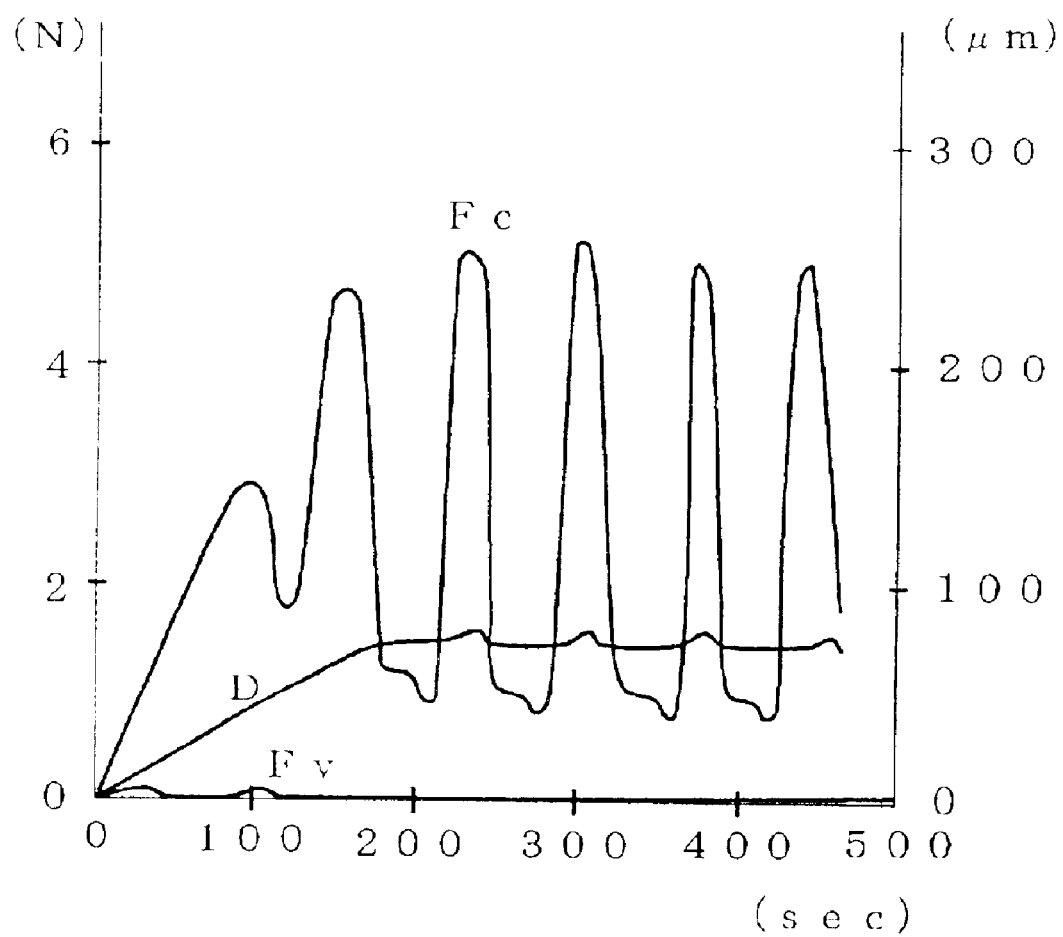
FIG. 6 is a graphic diagram showing profiles of change with time of the longitudinal load Fv, the cutting depth D, and the transverse load Fc.

FIG. 6 illustrates a profile of change with time of the longitudinal load Fv, the cutting depth D, and the transverse load Fc.

The transverse load Fc alternates between increase and decrease. The transverse load Fc is increased when the peeling stops, as shown in FIG. 4, and decreased when the peeling C runs instantly as shown in FIG. 5. This is repeated as the cutting action goes.

The cutting depth D is kept uniform as close to the interface B.

The longitudinal load Fv stays almost zero when the depth D is uniform.

The breaking strength of the sample S having a layered structure can be estimated from the maximum, minimum, amplitude, cycle, and average of the transverse load Fc.

Second Procedure
(1) The sample S is held by the sample holder 2 with its front side extending vertical.
(2) An automatic transverse load tracing action is initiated by the input unit 50.
(3) The longitudinal slide way 4 is moved in the first direction d1 by a combination action of the longitudinal driving motor 11 and the longitudinal ball screw 10 which is determined by the cutting depth controller 30m. This allows the longitudinal load slide way 6 to advance in the first direction d1 and thus the cutting blade 7 to cut into the sample S. The transverse slide way 3 is moved in the second direction d2 by a combination action of the transverse driving motor 9 and the transverse ball screw 8. As a result, the cutting blade 7 advances in the second direction d2. The cutting blade 7 is controlled to a desired depth by the cutting depth controller 30m so that the longitudinal load Fv alternates between increase and decrease. The depth is increased or decreased in steps of 2 μm.
(4) As the longitudinal load Fv, the cutting depth D, and the transverse load Fc measured at the above process (3) are expressed in a graphic profile of change with time and displayed on the monitor 40 or plotted down by a printer 60, they can be examined for further estimation.

Third Procedure
(1) The sample S is held by the sample holder 2 with its front side extending vertical.
(2) The number of interfaces (including the top surface) from the top surface to a target interface to be measured in the sample S is determined as the number of longitudinal load lowermost points. For example, when the sample S is a four-coating sheet of iron ranging from the first coating to the fourth coating and its interface between the second coating and the third coating is to be examined, the number of longitudinal load lowermost points is set to 3.
(3) The longitudinal slide way 4 is moved in the first direction d1 by a combination action of the longitudinal driving motor 11 and the longitudinal ball screw 10 which is determined by the cutting depth controller 30m. This allows the longitudinal load slide way 6 to advance in the first direction d1 and thus the cutting blade 7 to cut into the sample S.

(4) The transverse slide way 3 is moved in the second direction d2 by a combination action of the transverse driving motor 9 and the transverse ball screw 8. As a result, the cutting blade 7 advances in the second direction d2.

(5) The two processes (3) and (4) are continued until the number of longitudinal load lowermost points reaches a setting value. When the number of longitudinal load lowermost points reaches the setting value, the process (4) is carried out while controlling the cutting depth D similar to the first and second procedures. Then, the longitudinal load Fv, the cutting depth D, and the transverse load Fc are expressed in a graphic profile of change with time as displayed on the monitor 40 and can be examined for further estimation.

Fourth Procedure (1) The sample S is held by the sample holder 2 with its front side extending vertical.

(2) The depth from the top surface to an interface to be examined of the sample S is designated as the cutting depth.

(3) The longitudinal slide way 4 is moved in the first direction d1 by a combination action of the longitudinal driving motor 11 and the longitudinal ball screw 10 which is determined by the cutting depth controller 30m. This allows the longitudinal load slide way 6 to advance in the first direction d1 and thus the cutting blade 7 to cut to the setting depth in the sample S.

(4) The transverse slide way 3 is moved in the second direction d2 by a combination action of the transverse driving motor 9 and the transverse ball screw 8. As a result, the cutting blade 7 advances in the second direction d2.

(5) The process (4) is continued while the cutting depth D being controlled to stay at its setting depth. Then, the longitudinal load Fv, the cutting depth D, and the transverse load Fc are expressed in a graphic profile of change with time as displayed on the monitor 40 and can be examined for estimation.

As set forth above, the layered structure breaking strength estimating apparatus 100 has the following advantages.

(1) The criterion for estimating the breaking strength of the layered structure of the sample S can be obtained.

(2) The estimation can be implemented even when the layered structure has a higher level of the bonding strength.

(3) The estimation can be implemented even when the interface between layers is obscure.

(4) The relationship between the longitudinal load Fv, the cutting depth D, and the transverse load Fc can precisely be recognized.

(5) As the cutting blade 7 horizontally cuts into the sample S, its weight will hardly be exerted on the sample S. Therefore, no extra unit balancing device to apply a counter load will be needed.

The method of layered structure breaking strength estimation according to the present invention provides a new criterion for estimating the breaking strength of a layered structure having an upper layer and a lower layer. For example, this method will particularly be useful for estimating the strength of coatings of an automobile or an enclosure.

What is claimed is:

1. A method for layered structure breaking strength estimation, comprising:

inserting an edge of a cutting blade into an upper layer of the structure, moving the cutting blade substantially in parallel with an interface between the upper layer and a lower layer of the structure while automatically controlling a depth of the cutting blade to a depth slightly higher than the interface, the step of moving the cutting blade while automatically controlling the depth of the cutting blade comprises mounting the cutting blade on a longitudinal slide way, moving the longitudinal slide way in a direction vertical to the interface by means of a longitudinal ball screw and coupling a motor to the longitudinal ball screw to enable automatic control of the movement of the cutting blade in the direction vertical to the interface and thus the depth of the cutting blade, and measuring a force exerted on the cutting blade substantially in parallel with the interface.

2. A method for layered structure breaking strength estimation according to claim 1, wherein the force exerted on the cutting blade substantially in parallel with the interface, a force exerted on the cutting blade substantially vertical to the interface, and the depth of the cutting blade are expressed in the form of a graphic profile of change with time.

3. A method for layered structure breaking strength estimation according to claim 1 or 2, wherein the depth of the cutting blade is automatically controlled to increase or decrease by a unit of displacement not greater than 2 micrometer.

4. A method for layered structure breaking strength estimation according to claim 1, wherein the cutting blade is moved while automatically controlling the depth of the cutting blade to be constant.

5. A method for layered structure breaking strength estimation according to claim 1, further comprising measuring a variable force exerted on the cutting blade substantially vertical to the interface while maintaining the cutting depth constant.

6. A method for layered structure breaking strength estimation according to claim 1, further comprising arranging a first motor to move the cutting blade in a direction parallel to the interface and arranging a second motor separate from the first motor to move the cutting blade in a direction vertical or perpendicular to the interface.

7. A method for layered structure breaking strength estimation according to claim 1, further comprising adjusting the depth of the cutting blade by controlling the motor to actuate the longitudinal ball screw.

8. A layered structure breaking strength estimation apparatus comprising:

a cutting blade, inserting means for inserting an edge of the cutting blade into an upper layer of the structure, moving means for moving the cutting blade substantially in parallel with an interface between the upper layer and a lower layer of the structure, control means for automatically controlling a depth of the cutting blade to a depth slightly higher than the interface, said control means comprise a longitudinal slide way on which the cutting blade is mounted, a longitudinal ball screw arranged to move the longitudinal slide way in a direction vertical to the interface, and a motor coupled to the longitudinal ball screw to enable automatic control of the movement of the cutting blade in the direction vertical to the interface and thus the depth of the cutting blade, and measuring means for measuring a force exerted on the cutting blade substantially in parallel with the interface.

9. A layered structure breaking strength estimation apparatus according to claim 8, further comprising graphic means for expressing the force exerted on the cutting blade substantially in parallel with the interface, a force exerted on the cutting blade substantially vertical to the interface and the depth of the cutting blade in the form of a graphic profile of change with time.

10. A layered structure breaking strength estimation apparatus according to claim 8 or 9, wherein the depth of the cutting blade is automatically controlled to increase or decrease by a unit of displacement not greater than 2 micrometer.

11. A layered structure breaking strength estimation apparatus according to claim 8, wherein the cutting blade is moved by the moving means while the depth of the cutting blade Is automatically controlled to be constant by the control means.

12. A layered structure breaking strength estimation apparatus according to claim 8, further comprising measuring means for measuring a variable force exerted on the cutting blade substantially vertical to the interface while the cutting depth is maintained constant by the control means.

13. A layered structure breaking strength estimation apparatus according to claim 8, further comprising a first motor arranged to move the cutting blade in a direction parallel to the interface, and a second motor separate from the first motor arranged to move the cutting blade in a direction vertical or perpendicular to the interface.

14. A layered structure breaking strength estimation apparatus according to claim 8, wherein the motor is controlled to actuate the longitudinal ball screw and thereby adjust the depth of the cutting blade.

\* \* \* \* \*

UNITED STATES PATENT AND TRADEMARK OFFICE
CERTIFICATE OF CORRECTION

PATENT NO. : 6,792,812 B2
DATED : September 21, 2004
INVENTOR(S) : Yoshio Kishima et al.

It is certified that error appears in the above-identified patent and that said Letters Patent is hereby corrected as shown below:

Title page,
Item [73], Assignees, "Diapola Wintes Co., Ltd., Saitama (JP)" should read
-- Daipola Wintes Co., Ltd., Saitama (JP) --.

Signed and Sealed this

Third Day of May, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,792,812 B2 |
| APPLICATION NO. | : 10/033434 |
| DATED | : September 21, 2004 |
| INVENTOR(S) | : Yoshio Kishima et al. |

It is certified that error appears in the above-identified patent and that said Letters Patent is hereby corrected as shown below:

Title page,
Item [73], Assignees, "Diapola Wintes Co., Ltd., Saitama (JP)" should read
-- Daipla Wintes Co., Ltd., Saitama (JP) --.

This certificate supersedes Certificate of Correction issued May 3, 2005.

Signed and Sealed this

Twenty-second Day of May, 2007

JON W. DUDAS
*Director of the United States Patent and Trademark Office*